United States Patent
Marchand et al.

(10) Patent No.: US 9,551,701 B2
(45) Date of Patent: Jan. 24, 2017

(54) METHOD FOR DETECTING ANALYTE IN A BODILY FLUID, AND DRESSING FOR IMPLEMENTING SUCH A METHOD

(75) Inventors: Gilles Marchand, Pierre-Chatel (FR); Pierre Marcoux, Sassenage (FR)

(73) Assignee: COMMISSARIAT À L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 0 days.

(21) Appl. No.: 13/520,078

(22) PCT Filed: Dec. 29, 2010

(86) PCT No.: PCT/FR2010/000882
§ 371 (c)(1),
(2), (4) Date: Jun. 29, 2012

(87) PCT Pub. No.: WO2011/080427
PCT Pub. Date: Jul. 7, 2011

(65) Prior Publication Data
US 2012/0283529 A1    Nov. 8, 2012

(30) Foreign Application Priority Data
Jan. 4, 2010  (FR) ..................... 10 00007

(51) Int. Cl.
*G01N 33/00* (2006.01)
*G01N 33/50* (2006.01)
(Continued)

(52) U.S. Cl.
CPC ............. *G01N 33/5088* (2013.01); *A61B 5/00* (2013.01); *A61F 13/0213* (2013.01);
(Continued)

(58) Field of Classification Search
CPC .. G01N 33/5088; A61F 13/0273; A61F 15/56; A61F 2013/429
See application file for complete search history.

(56) References Cited

U.S. PATENT DOCUMENTS 4,548,906 A    10/1985  Sekikawa et al.
4,732,153 A *  3/1988  Phillips ........................ 600/367
(Continued)

FOREIGN PATENT DOCUMENTS

CA    2 497 724 A1    2/1998
EP    0 430 608 A1    6/1991
(Continued)

OTHER PUBLICATIONS

Miller et al., "Spot Indole Test: Evaluation of Four Reagents," *Journal of Clinical Microbiology*, Vo. 15, No. 4, pp. 589-592, Apr. 1982.
(Continued)

*Primary Examiner* — Sam P Siefke
(74) *Attorney, Agent, or Firm* — Oliff PLC

(57) ABSTRACT

A method for detecting an analyte in a bodily fluid includes placing the detector in contact with at least one metabolite resulting from the metabolism or degradation of the analyte. The contact between the detector and the metabolite produces an optically detectable signal. The detection method includes the detection of the metabolite only in gas form, said metabolite in gas form coming from the evaporation of at least a part of said metabolite. The detection is also carried out without contact between the bodily fluid and the detector. A dressing for implementing the detection method is also described.

15 Claims, 3 Drawing Sheets

(51) Int. Cl.
*A61B 5/00* (2006.01)
*A61L 15/56* (2006.01)
*A61F 13/02* (2006.01)
*A61F 13/00* (2006.01)

(52) U.S. Cl.
CPC .......... *A61F 13/0226* (2013.01); *A61L 15/56* (2013.01); *A61F 13/0273* (2013.01); *A61F 2013/00429* (2013.01); *A61F 2013/00846* (2013.01); *A61F 2013/00965* (2013.01)

(56) References Cited

U.S. PATENT DOCUMENTS

| | | | |
|---|---|---|---|
| 5,181,905 A | 1/1993 | Flam | |
| 5,445,147 A * | 8/1995 | Schoendorfer et al. | 600/362 |
| 5,899,856 A | 5/1999 | Schoendorfer et al. | |
| 5,910,447 A | 6/1999 | Lawrence et al. | |
| 6,981,947 B2 * | 1/2006 | Melker | 600/532 |
| 7,364,918 B2 | 4/2008 | Prince | |
| 8,256,286 B2 * | 9/2012 | Carroll et al. | 73/335.04 |
| 2002/0091347 A1 | 7/2002 | Eakin | |
| 2004/0236199 A1 * | 11/2004 | Hawthorne et al. | 600/345 |
| 2006/0153740 A1 * | 7/2006 | Sultan et al. | 422/88 |
| 2007/0142762 A1 | 6/2007 | Kaplan et al. | |
| 2007/0258860 A1 | 11/2007 | Tanaka | |

FOREIGN PATENT DOCUMENTS

| | | |
|---|---|---|
| EP | 1 790 982 | 5/2007 |
| WO | WO 02/30478 A2 | 4/2002 |

OTHER PUBLICATIONS

Allardyce et al., Detection of volatile metabolites produced by bacterial growth in blood culture media by selected ion flow tube mass spectrometry (SIFT-MS), *Journal of Microbiological Methods*, vol. 65, pp. 361-365, 2006.

Loiseau et al., "A fluoroponytails containing organogelator: gelation of perfluorotributylamine and isopropopanol," *Tetrahedron*, vol. 58, pp. 4049-4052, 2002.

International Search Report issued in Application No. PCT/FR2010/000882; Dated Mar. 17, 2011 (With Translation).

* cited by examiner

METHOD FOR DETECTING ANALYTE IN A BODILY FLUID, AND DRESSING FOR IMPLEMENTING SUCH A METHOD

TECHNICAL FIELD OF THE INVENTION

The invention relates to a method for detecting an analyte in a bodily fluid as well as a dressing for implementing such a method.

STATE OF THE ART

A lot of works has been carried out for detecting in a qualitative way the presence of a analyte in a bodily fluid.

For a few years, colorimetry techniques have been used in the medical field in particular to meet a need for determining the evolution of a wound and for describing the germs developing in the wound exudate.

Originating in the classification of bacteria, the Gram test is a widespread method which makes it possible to identify and to differentiate bacteria thanks to a staining test in solution. This method requires to take a sample of bodily fluid and then to subject it to a Gram test in vitro. This test is based on the characteristics of the membranes and walls of bacteria.

Other colorimetric indicators are used to detect not the bacterium itself but one or more products generated during the growth of the bacterium. Thus, in the article "Spot Indol Test: Evaluation of Four Reagents" (Journal of Clinical Microbiology, 1982, 589-592), J. M. Miller and al. describes a paper impregnated with a solution containing Kovacs reagent. Kovacs reagent is known for detecting so-called "indole positive" bacteria in a solution. These bacteria generate indole during their growth, which is a by-product of the hydrolysis of tryptophan by tryptophanase. The compound dimethyl-amino-4-benzaldehyde contained in Kovacs reagent reacts with indole to form a red-colored compound.

Recently, dressings based on various types of indicators have been proposed. The dressings used for wounds must be changed at regular intervals, for example, in order to maintain a certain humidity favoring wound healing and to keep clean the wound and the parts surrounding the wound or to change the type of dressing used according to the healing step of the wound.

During the healing process, the follow-up of the evolution of a wound is a great part of the daily work of a medical staff because it makes it possible to know, in particular, the healing state of the wound and provides an indication on when a dressing must be replaced. The wounds concerned are, for example, bedsores, diabetic wounds, wounds formed by an ulcer, a burn, a surgical procedure or a transplant, skin tumors or genetic diseases. Wounds are usually checked by looking approximately for the presence of visual and odorous cues. In the case of an important bacterial load within a wound, a lot of inflammatory signs characteristic of an infection and an inflammatory defense reaction of a body appears: an exudate which is abundant, thick, even nauseous and colored according to the present germ, perilesional erythema with a spontaneous pain and an edematous reaction.

The document US-A-2002091347 describes a dressing able to indicate when it must be changed according to the moisture content of the dressing. This dressing successively includes an external coating, a waterproof layer, a calorimetric indicator and a dressing lining. The dressing lining has the form of a layer intended to be in contact with the wound and is waterproof until it is saturated with water and becomes then permeable to water. Water then flows through the dressing and reaches the colored indicator which changes color when in contact with water.

Other dressings have been proposed whose purpose is to detect a rise in temperature characteristic of an infection. These works are based on the principle that the application of a dressing on a zone of the skin or of a wound involves an increase in the temperature in this zone. The accumulation of metabolites in a confined space, combined with an increase in the pressure around said zone due to the presence of the dressing, causes an inrush of blood responsible for the rise in temperature. The document U.S. Pat. No. 5,181,905 discloses, for example, a dressing including an indicator of temperature consisting of a temperature detection band containing liquid crystals.

This approach has the disadvantage to be not very discriminating as for the causes of this rise in temperature, in particular as for the nature of the metabolites present in said zone and, consequently, as for the need for changing or not the dressing.

The document U.S. Pat. No. 7,364,918 proposes a colorimetric sensor containing polydiacetylene assemblies and a receiver as well as a method for using this sensor for detecting a analyte. The receiver is selected to specifically interact with the analyte. This receiver is incorporated into a ene-yne polymeric network conjugated before or after the polymerization. The thus-formed structure of the conjugated polymer is able to change its conformation according to the interactions of the receiver with the analyte. Disturbances induced on the structure of the conjugated polymer skeleton then involve a change of color. The colorimetric sensor can indicate, for example, the presence of Gram-negative and Gram-positive bacteria in biological liquids. The authors also propose to combine this colorimetric sensor with a dressing for detecting the presence of an infection, for example, by integrating it into a dressing in the form of a layer in direct or indirect contact with the wound, but according to this document, the sensor is always in contact with the exudate. Nevertheless, a sensor based on a simple conformational change of a polymer can involve a significant number of false positive results.

Other works have been carried out for detecting, more largely, the presence of a analyte in a bodily fluid taken from an individual such as a vaginal fluid, blood or urine. For example, the documents U.S. Pat. No. 5,910,447, U.S. Pat. No. 4,548,906 and US-A-2007258860 can be cited which propose detectors and methods for detecting ammonia or amines in gas form.

The document U.S. Pat. No. 5,899,856 which describes a method for detecting ethanol or an ethanol metabolite from the sweat perspired by an individual can also be cited. The method comprises, in particular, the collection of ethanol thanks to a dermal patch placed on the skin, for absorbing perspired ethanol, then the desorption extraction of ethanol or of the metabolite contained in the dermal patch followed by the analysis of the extracted liquid.

Nevertheless, the solutions suggested are not applicable directly to an individual for a real-time analysis.

OBJECT OF THE INVENTION

The purpose of the invention is to propose a method for detecting the presence of an analyte in a bodily fluid, giving a reliable and precise qualitative information, and able to be implemented outside a laboratory.

The purpose of the invention is also to propose a dressing for implementing this method, which is inexpensive and gives a reliable, precise and fast indication on the presence of a analyte in a bodily fluid.

According to the invention, this purpose is reached by a detection method and a dressing for implementing such a method according to the annexed claims.

In particular, this purpose is reached in that a detector is placed above a zone of an individual's or an animal's skin containing the bodily fluid, in that at least one metabolite resulting from the metabolism or degradation of the analyte is then detected, only in gas form, by placing the detector in contact with the gas metabolite, said gas metabolite coming from the evaporation of at least a part of said metabolite and said contact producing an optically detectable signal and in that the detection is carried out without contact between the bodily fluid and the detector.

BRIEF DESCRIPTION OF THE DRAWINGS

Other advantages and characteristics will more clearly arise from the following description of particular embodiments of the invention given as nonrestrictive examples and represented in the annexed drawings, in which.

Figure 1:
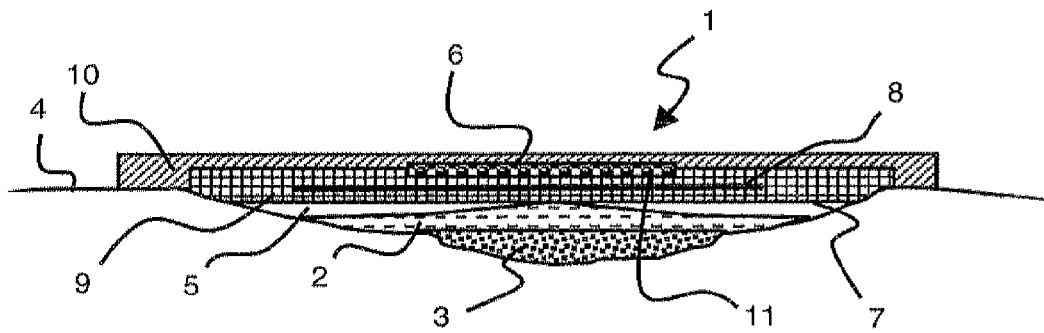
FIGS. 1 to 5 are a schematic and sectional representation of various particular embodiments of a dressing according to the invention.

DESCRIPTION OF PARTICULAR
EMBODIMENTS OF THE INVENTION

According to one particular embodiment, a method for detecting an analyte in a bodily fluid comprises the positioning of a detector above a zone of an individual's or animal's skin containing the bodily fluid and then the detection of at least one metabolite, only in gas form, resulting from the metabolism or the degradation of the analyte. The detection is carried out by bringing the detector, placed above the zone of the skin containing the bodily fluid, in contact with the gas metabolite. The gas metabolite detected comes from the evaporation of at least a part of the metabolite. The contact of the detector with the gas metabolite(s) produces an optically detectable signal. The detection is carried out without contact between the bodily fluid and the detector. Indeed, the bodily fluids are likely to contain many analytes which could interact with the detector if the latter were in contact with the bodily fluid. That could generate false positive results. One thus may find it beneficial to avoid any contact between the bodily fluid and the detector. Moreover, the absence of contact avoids any contamination of the bodily fluid by a substance contained in the detector.

The bodily fluid can be, for example, sweat, blood, tears, vaginal secretions, lymph, saliva, urine, or the exudate of a wound of an individual's or animal's skin. In particular, the bodily fluid consists in an exudate from a wound of an individual's or animal's skin.

The term "analyte" includes, without any limitation, pathogenic and nonpathogenic organisms, enzymatic substrates, antibodies, antigens, proteins, peptides, bacteria, viruses, protozoa, enzymes, amino acids, lipids, sugars, hormones, parasites or fungi or the components of the bodily fluid. One can also add small molecules such as urea, the term small molecules indicating the molecules whose molecular weight is lower than 500 g/mol.

The analyte is, advantageously, a bacterium. As an indication and in a nonrestrictive way are cited gram-positive bacteria of the *Staphylococcus* type such as *Staphylococcus aureus* or gram-negative bacteria of the *Pseudomonas* type such as *Pseudomonas aeruginosa* and the so-called "indole positive" bacteria of the *Escherichia* type such as *Escherichia coli*.

Certain families of bacteria are well-known to be able to generate metabolites during their growth. A certain number of these metabolites are volatile i.e. have a tendency to evaporate, for example, in contact with air. Thus, in the article "Detection of volatile metabolites produced by bacterial growth in blood culture media by selected ion flow tube mass spectrometry (SIFT-MS)", (Microbiol. Methods, 2006, 65, 361-365), Allardyce r.a. and al, have shown the production of metabolites during the metabolism of golden staphilococca, in particular metabolites such as ethanol, acetone, acetaldehyde, ammonia, acetic acid, dimethyl sulfide, methane thiol, sulfured dihydrogene, indole, aminoacetophenone, trimethylamine and hexanal. In the same way, it has been shown that *Pseudomonas aeruginosa* emits dimethyl sulfide, methane thiol and sulfured dihydrogene.

In addition, the so-called "indole positive" bacteria such as *Escherichia coli, Aeromonas hydrophilia* and some Citrobacters are also known to generate, during their growth, indole which is also a volatile product.

The emission of these volatile metabolites produced during the metabolism of the bacterium can constitute a true fingerprint or signature of the bacterium. Under volatile metabolite it is understood any metabolite likely to turn to a gas state.

Other analytes present in a bodily fluid can also be degraded, for example by oxidation or under the action of bacteria or of enzymes, and then release one or more volatile metabolites. As an example, urea can be cited which is present in sweat and can break up into ammonia and carbon dioxide.

The volatile metabolite resulting from the metabolism or the degradation of the analyte is, advantageously, a volatile organic compound or "VOC".

Thus, by detecting the gas metabolite(s) resulting from the metabolism or the degradation of the analyte, it is possible to detect the presence of the analyte if this metabolite or the combination of metabolites is specific to the analyte. By using a specific detector, one can also detect metabolites of the same family of compounds, for example, ethanol and methanol or putrescine and cadaverine or $H_2S$ and $CH_3SH$.

According to one particular embodiment, to favor detection, a first step of the detection method consists in forming a confined space by applying an element of confinement comprising the detector above a zone of an individual's or animal's skin containing the bodily fluid. The detector is preferably placed above the zone of an individual's or animal's skin containing the bodily fluid.

Under confined space it is understood a space delimited by the element of confinement and the zone of the individual's or animal's skin. On the other hand, this term does not necessarily imply that there is an empty space between the element of confinement and the bodily fluid. The element of confinement can be in contact with the bodily fluid: thus, the bodily fluid does not come into contact with the detector.

The element of confinement can be at least partly permeable to certain gas species.

At least a part of the metabolite resulting from the metabolism or degradation of the analyte gradually evaporates after applying the element of confinement onto the skin. The part of the not-evaporated metabolite remains in the bodily fluid in a dissolved form. The increase in the concentration of the metabolite in gas form relative to the concentration of the same metabolite in liquid form depends on several parameters, in particular, on the nature of the metabolite, the dimensions of the element of confinement and the quantity of bodily fluid. This concentration depends on the Henry's law expressing a ratio of the concentration of a species in liquid phase to the concentration of this same species in gas phase.

The metabolite in gas form penetrates in the confined space until coming into contact with the detector.

The contact between the detector and the gas metabolite produces an optically detectable signal. Under optically detectable it is understood any perceptible sign, which can be observed or read, directly or indirectly, by an optical means. During the contact, the detector and the gas metabolite interact together. This interaction is responsible for a modification of the optical properties of the detector.

The detector is advantageously specific to one or more metabolites to be analyzed i.e. it produces one or more optically detectable signals when in contact with the metabolite(s) to be analyzed present in a gas form. The detector advantageously produces a signal proportional to the quantity of metabolite in contact for a qualitative and quantitative analysis.

The detector is preferably selected between a chromogene detector or a fluorogene detector. The interaction induced by the contact of the gas metabolite with the detector causes a modification of the emission or absorption spectrum. A reaction of a covalent type between the gas metabolite and the detector is privileged because it enables to generate at least one covalent bond, which is stable in the time, and avoids any loss of information in the course of time. In the same way, the interaction of the covalent type between the gas metabolite and the detector can cause a more important modification of the spectrum than in the case of the creation of weak bonds, for example, of the van der Waals type, thus improving the sensitivity of the detector.

In the case of a chromogene detector, the contact of the gas metabolite with the detector produces a change of color of at least a part of the detector. The chromogene detector has the advantage of directly reading, to the naked eye, the presence or not of the analyte in the bodily fluid.

In the case of a fluorogene detector, the contact of the gas metabolite with the detector produces a fluorescent emission of at least a part of the detector. In this case, a means for exciting fluorescence, in particular an adapted source of light such as a UV lamp, can be necessary to detect the radiation of fluorescence.

According to a particular embodiment, the detector comprises a probe sensitive to the metabolite and a support. Under probe it is understood any molecule or substance having an affinity of connection for a target. The probe is in particular responsible for the chromogene or fluorogene property of the detector such as described above.

The probe has one or more functions which interact with the metabolite constituting the target so that, once bound to the metabolite, the probe produces an optically detectable signal. The probe preferably reacts with at least one metabolite in an irreversible and selective way, preferably by covalent bond. The reaction of the probe and the metabolite advantageously forms an absorbing or fluorescent compound. The fluorogene detector generally has the advantage of a greater sensitivity.

The probe can be specific to a volatile metabolite or a class of metabolites having a particular function or reactivity. The ability of the probe to interact with a target depends on the metabolite constituting the target. According to the metabolite to be detected, the man skilled in the art is able to determine the known probe to be used and is able to implement the steps of synthesis and/or insertion in the support and/or grafting onto the support according to any known method in order to obtain the suitable detector.

As a first example, the probe can be 4-Aminopent-3-in-2-one which is a compound known to detect light aldehydes such as formaldehyde, in the form of volatile organic compounds (VOCs) present in the air. As an example, 4-Aminopent-3-in-2-one reacts with formaldehyde according to the following reaction (1):

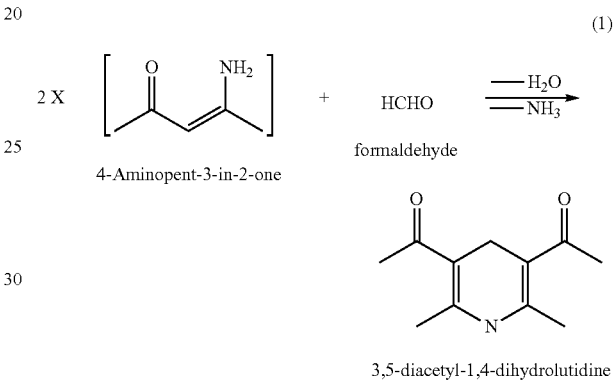

The obtained compound 3,5-diacetyl-1,4-dihydrolutidine is fluorescent.

In addition, the compound 4 (dimethylaminobenzaldehyde) (noted "DMABA") called James' reagent and the compound 4-dimethylaminocinnamaldehyde (noted "DMACA") called Kovacs' reagent make it possible to detect indole in solution, respectively, according to the following reactions (2) and (3):

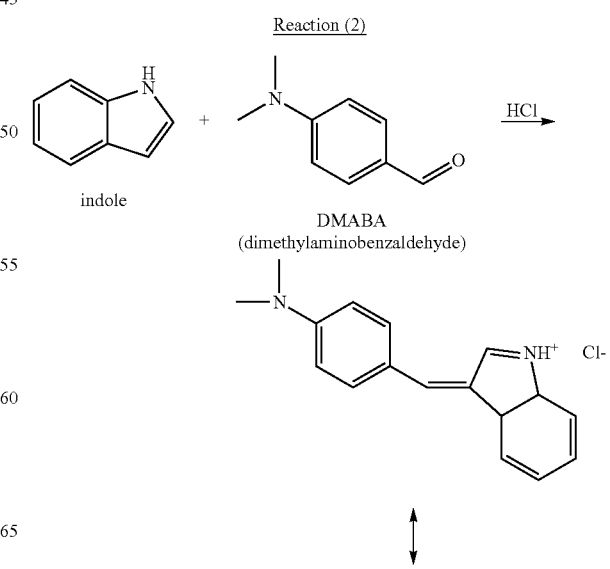

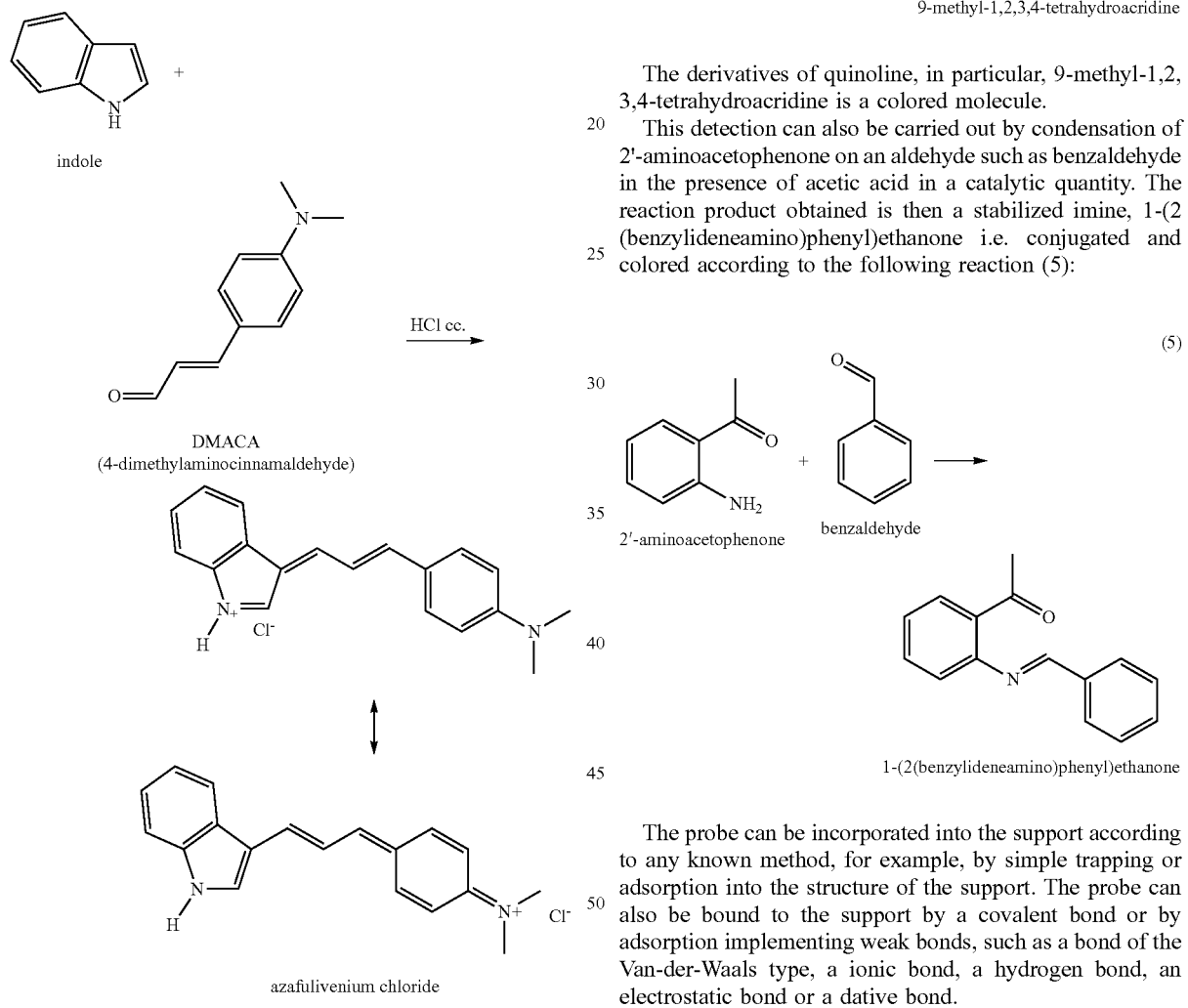

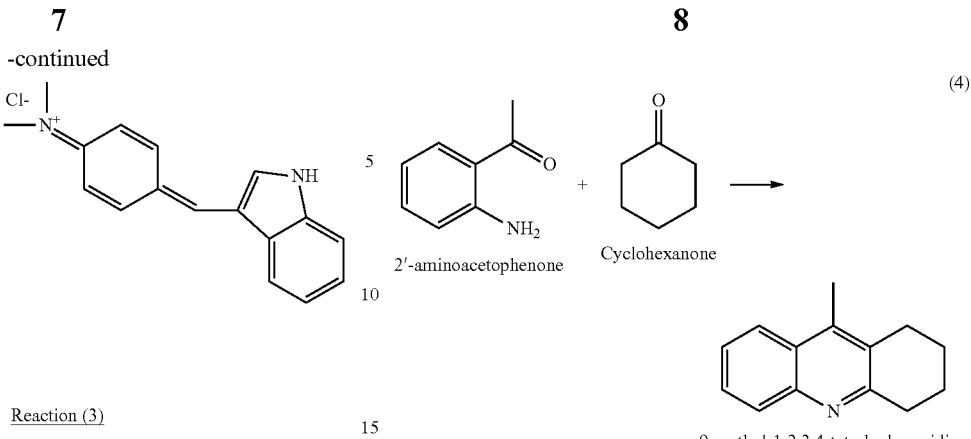

The derivatives of quinoline, in particular, 9-methyl-1,2,3,4-tetrahydroacridine is a colored molecule.

This detection can also be carried out by condensation of 2'-aminoacetophenone on an aldehyde such as benzaldehyde in the presence of acetic acid in a catalytic quantity. The reaction product obtained is then a stabilized imine, 1-(2 (benzylideneamino)phenyl)ethanone i.e. conjugated and colored according to the following reaction (5):

The interaction between the target indole and a probe of the DMABA or DMACA type leads to azafulivenium chlorides, which are absorbing products.

As a second example, the probe can be the compound 2'-aminoacetophenone known as a specific volatile organic compound of *Pseudomonas aeruginosa*. The detection of 2'-aminoacetophenone can be carried out by the Friedländer reaction. Indeed, the compound 2'-aminoacetophenone reacts with cyclohexanone in the presence of acetic acid in a catalytic quantity, to give a derivative of quinoline according to the following reaction (4):

The probe can be incorporated into the support according to any known method, for example, by simple trapping or adsorption into the structure of the support. The probe can also be bound to the support by a covalent bond or by adsorption implementing weak bonds, such as a bond of the Van-der-Waals type, a ionic bond, a hydrogen bond, an electrostatic bond or a dative bond.

According to an alternative, the probe can consist in the support itself, in particular when the volatile metabolite is colored. Its adsorption on the support then involves a modification of the absorption spectrum of the support.

The support is advantageously transparent or translucent to facilitate the reading of the result of the detection.

The support is preferably permeable to the metabolite in gas form. The support is advantageously a porous support in order to allow a better diffusion of the metabolite within the support and to favor the contact of the metabolite with the probe. The porosity of the support also makes it possible to control the diffusion of the gaseous species within the detector in particular by ensuring the sort according to the size of the different gaseous metabolites. The porosity of the support is a parameter which can have a role in the selectivity of the detection.

The support is advantageously a polymer. Under polymer it understood soluble and insoluble polymers as well as copolymers. The support can be selected among organic polymers. For example, the support can be a macroporous resin such as a macroporous polystyrene resin. Preferably, the polymer is selected among known not-poisonous and/or biocompatible polymers.

It can also be a porous oxide, a preferably nonmetal one, for example containing silicon oxide.

According to a particular embodiment, the support is a porous polymer in order to allow the circulation of the metabolite in gas form through the polymeric skeleton.

The specific surface of the porous polymer is preferably higher than or equal to 50 $m^2/g$, preferably higher than or equal to 500 $m^2/g$, in order to increase the probability of interaction between the probe and the metabolite in gas form and thus to improve the sensitivity of the detection.

The probe can be bound to the polymer forming the support by a covalent bond, according to any known method, for example by post-functionalization of a polymer or copolymerization of monomers that have been functionalized beforehand.

According to another particular embodiment, the support is a polymer with a strong ability to solubilize gaseous compounds. Thus, in addition to the role of support, the polymer can also be used for absorbing and/or storing gaseous metabolites. Thus, at least a part of the metabolite, in gas form, in contact with the detector, can be solubilized in the polymer and then react with the probe in a solubilized form.

The polymer is preferably selected among any known gel polymer with a good ability to dissolve gases such as strongly hydrated polymers.

The polymer is selected for example among a hydrogel such as agarose, a hydrogel, an alginate, a gel of hyaluronic acid, polydimethylsiloxane, cellulose, polyethylene glycol, poly(vinyl alcohol) (noted "PVA"), poly(propylene fumarate), poly(alpha-hydroxyesters), poly(orthoesters), polyanhydrides, poly(phosphazenes), poly(propylene fumarate), poly(ester amides), poly(ethylene fumarate), polylactic acide, polyglycolic acid, polycaprolacton (noted "PCL"), and polydioxanone (noted "PDO"), polyurethane and carboxylmethylcellulose.

The gel polymer is advantageously selected among an alginate, a hydrogel, a gel polymer containing silicone oil and a fluorinated or silicone organogel, such as a gel of Cholesteryl anthraquinone-2-carboxylate and of polymethylsiloxane, or a gel of 1,3:2,4-dibenzylidene-Sorbitol and octamethylcyclotetrasiloxane or an gel of aromatic diamide with a perfluorinated chain and perfluorotributylamine, such a gel being described in the publication of J. Loiseau et al. (Tetrahedron, 2002, 4049-4052).

According to a preferential embodiment represented in FIGS. 1 to 5, the element of confinement comprises a dressing 1. In particular, the element of confinement can be a dressing 1. The bodily fluid 2 preferably consists of the exudate coming from a wound 3 of the skin 4. The dressing 1 is applied onto a zone of an individual's or animal's skin 4 containing the bodily fluid 2 in order to form a confined space 5. The confined space 5 is delimited by the dressing 1 (at the top of FIG. 1) and the individual's or animal's skin 4 covered by the dressing 1 (at the bottom of FIG. 1). The dressing 1 is integral with the skin 4.

As represented in FIGS. 1 to 5, the dressing 1 allowing the implementation of the above-described detection method comprises a detector 6, a covering face 7 for an individual or animal's skin 4 and means of protection 8 between the covering face 7 and the detector 6. The detector 6 is as described previously, in particular it is a chromogene or fluorogene detector.

More precisely, the confined space 5 is delimited by the covering face 7 of the dressing 1 and the surfaces of the skin 4 covered by the covering face 7. The detector 6 is located in or on the dressing 1 and is preferably arranged above the bodily fluid 2 in order to favor the contact of the metabolite in a volatile gas form with the detector 6.

The means of protection 8 are inert with respect to the metabolite, permeable to the metabolite in gas form and impermeable to the bodily fluid 2. The presence of the means of protection 8 makes it possible to avoid any contact between the bodily fluid 2 and the detector 6. The means of protection 8 constitute a physical barrier preventing the bodily fluid 2 from reaching the detector 6. The means of protection 8 are advantageously formed by at least one layer of one or more materials permeable to the metabolite in gas form and impermeable for the bodily fluid 2. Advantageously, the means of protection 8 comprise a layer of hydrophobic polymer, for example a polyurethane, this polymer being naturally hydrophobic.

According to a first particular embodiment represented in FIG. 1, the dressing 1 comprises a primary dressing 9, a secondary dressing 10 and the detector 6 located at the interface of the primary dressing and the secondary dressing, respectively 9 and 10. As represented in FIG. 1, the dressing 1 can be formed by a stack of adjacent layers successively comprising the secondary dressing 10, the detector 6 and the primary dressing 9 (from top to bottom in FIG. 1).

The primary dressing 9 is generally in contact or potentially in contact with the exudate. It can consist of a material chosen among: a woven or not woven textile such as tulle, viscose gauze, cotton, knitted polyamide fabric, polyester weft, a polymer or gel polymer such as polyurethane, carboxymethyl cellulose, alginate, collagen, gauze, acetate, viscose, activated carbon wrapped in a not woven sheet of textile, for example a piece of gauze. The primary dressing 9 can be a piece of woven and/or non-woven cotton gauze, possibly, hydrophilic. A piece of woven and non-woven cotton gauze constitutes a piece of wadded gauze.

The primary dressing 9 can provide one or more following functions: pumping of the bodily fluid 2, antibacterial function, hydration, healing, anti-odor.

The secondary dressing 10 primarily ensures essentially a retaining function. The secondary dressing 10 can include any known adhesive band or a conventional dressing. The secondary dressing 10 is advantageously transparent or translucent in order to allow a direct reading of the signal emitted by the detector 6. Thus, the reading of the presence or the absence of one or several analytes in the bodily fluid 2 can be carried out without removing the dressing 1 from the skin 4.

A dressing usually consists of such a primary dressing 9 and such a secondary dressing 10, the materials and functions of the primary dressing 9 and the secondary dressing 10 having been previously described.

In this first embodiment, the detector belongs to the primary dressing 9, means of protection also forming part of the primary dressing 9 preventing the bodily fluid 2 from migrating towards the detector 6.

In the following embodiments, one will see that the detector 6 can also belong to the secondary dressing 10, the means of protection being then arranged in the primary dressing 9 and/or the secondary dressing 10.

One will also see that, when the detector 6 is part of a primary dressing 9, the primary dressing 9 can be made of a same material, the detector 6 being placed in a first hydrophobic part of this material, the means of protection being made with a second hydrophilic part of this material.

According to a not represented alternative, the secondary dressing 10 has a transparent window opposite and above the detector 6 (at the top of FIG. 1), in order to be able to visualize with the naked eye the possible change of color of the detector 6 when the dressing 1 is applied to the skin 4.

The dressing 1 advantageously comprises the detector 6 with a detection face 11 opposite the bodily fluid 2, the covering face 7 opposite the bodily fluid 2 and the means of protection 8 for isolating the detector 6 from the bodily fluid 2.

As represented in FIG. 1, the means of protection 8 are arranged between the detection face 11 and the covering face 7 and are preferably placed below and opposite the detector 6 in order to constitute a physical barrier preventing the bodily fluid 2 from migrating towards the detector 6. Advantageously, the means of protection 8 are integrated into the primary dressing 9 (FIG. 1).

As represented in FIG. 1, the covering face 7 can be in contact with the bodily fluid 2, in particular when the detected bodily fluid 2 is exudate from a wound 3. In this case, the covering face 7 preferably covers the zone of the skin 4 where there is the wound 3.

The detector 6, preferably a chromogene or fluorogene detector 6, produces an optically detectable signal when in contact with at least one metabolite, in gas form, resulting from the metabolism or the degradation of the analyte contained in the bodily fluid 2 as described above.

As represented in FIG. 1, the detector 6 can consist of a layer deposited on the primary dressing 9 according to any known method, for example, as previously described by impregnation of a gel polymer containing a probe on the primary dressing 9, preferably a textile one. As an example, the detector 6 can be made by mixing at least the probe and the gel polymer and then by depositing the thus-obtained mixture onto the primary textile dressing 9 of the dressing 1. The primary dressing 9 is impregnated with the mixture probe/polymer which solidifies therein to form the detector 6.

The dressing 1 can also comprise several detectors 6, identical or different, specific to one or more metabolites for a multi-parametric detection, a better reproducibility and a better sensitivity of the results.

Figure 2:
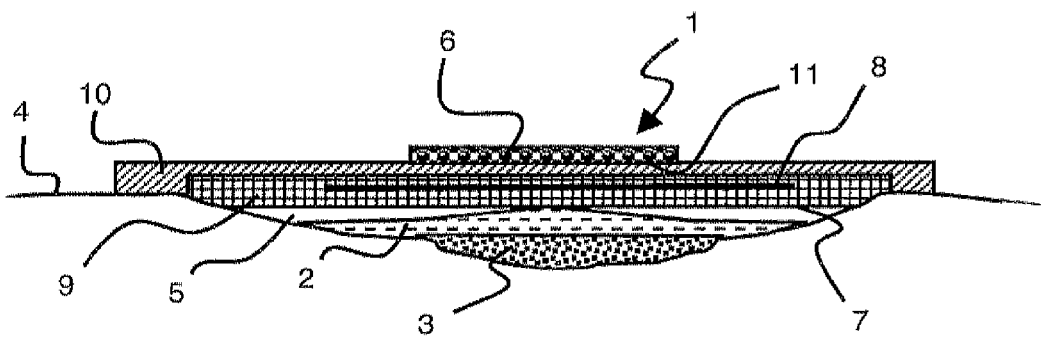

According to a second particular embodiment represented in FIG. 2, the dressing 1 is identical to the first particular embodiment (FIG. 1) except for the fact that the detector 6 is arranged on a face of the secondary dressing 10 which then constitutes the detection face 11. In this case, the secondary dressing 10 must be at least partly permeable to the metabolite in gas form.

Figure 3:
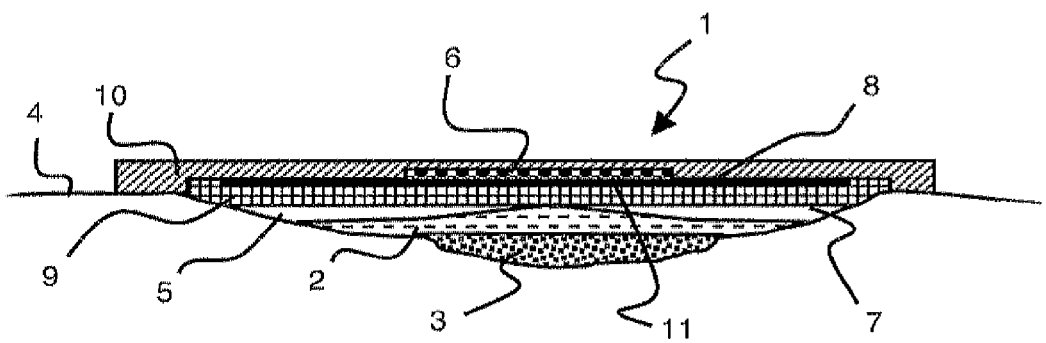

According to a third particular embodiment represented in FIG. 3, the dressing 1 is identical to that of the first embodiment (FIG. 1) except for the fact that the dressing 1 consists of a stack of adjacent layers comprising successively the secondary dressing 10, the detector 6, the means of protection 8 and the secondary dressing 10 (from top to bottom in FIG. 3). The detector 6 is arranged on the layer constituting the means of protection 8. The detection face 11 is then in contact with at least a part of the means of protection 8.

Figure 4:
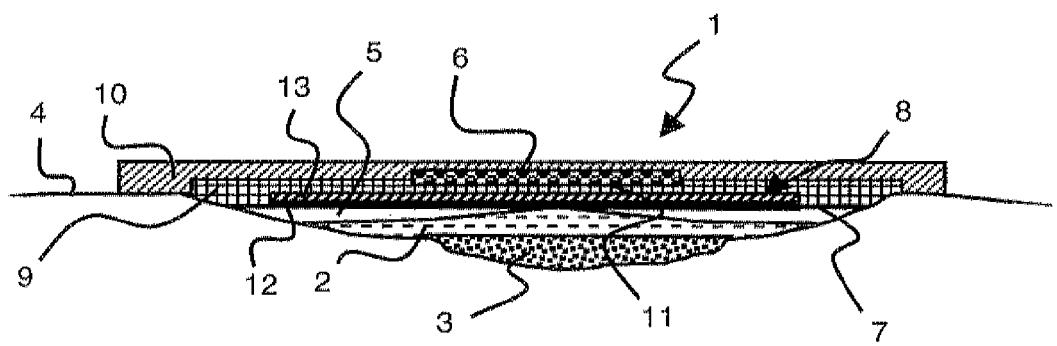

According to a fourth embodiment represented in FIG. 4, the dressing 1 is identical to that of the first embodiment (FIG. 1) except for the fact that the covering face 7 is advantageously made up, at least partly, of the means of protection 8. As an example, the means of protection 8 are formed by an external layer 12 of an hydrophilic polymer, for example a polyurethane made hydrophilic by any known means, and an internal layer 13 of a hydrophobic polymer such as a polyurethane, this material being naturally hydrophobic. The external layer 12 is intended to be in contact with the bodily fluid 2 on the individual's or animal's skin 4 and the internal layer 13 is arranged opposite the detector 6. The hydrophilic nature of the external layer 12 favors the interaction with the bodily fluid 2 and its impregnation inside the dressing 1 and advantageously makes it possible to bring the bodily fluid 2 closer to the detector 6 in the dressing 1. The hydrophobic nature of the internal layer 13 makes the means of protection 8 impermeable to the bodily fluid 2 and prevents the bodily fluid 2 from migrating towards the detector 6. The means of protection 8 consist for example of a polyurethane layer for constituting the internal layer 13. The polyurethane layer 13 protects the detector 6 by forming a physical barrier preventing the bodily fluid 2 from entering the primary dressing 9 beyond the protection layer while allowing the diffusion of the gaseous species.

Figure 5:
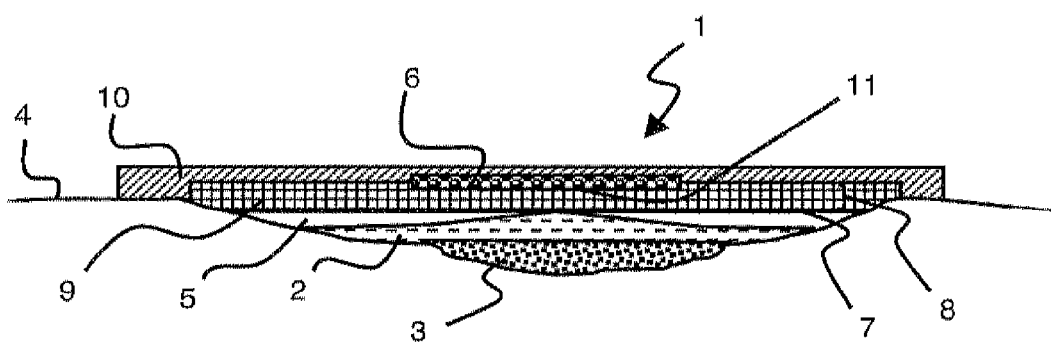

According to a fifth embodiment represented in FIG. 5, the embodiment differs from the other embodiments in that the means of protection 8 are advantageously formed by a lining thickness of the primary dressing 9. The lining then has the role of a physical barrier against the progression of the bodily fluid 2 within the dressing 1 and isolates the detector 6 from the bodily fluid 2. For a piece of woven gauze, the lining is classically formed by a succession of layers of woven gauze. The lining thickness of the primary dressing 9 must be important enough to constitute an obstacle to the impregnation of the bodily fluid 2 within the dressing 1 up to the detector 6. The lining can be locally made hydrophobic in the vicinity of the detector 6. The primary dressing 9 has a thickness advantageously comprised between 1 mm and 50 mm, preferably between 1 mm and 10 mm.

According to another example, the primary dressing consists of polyurethane, the means of protection consisting of polyurethane made hydrophilic, the other part, containing the detector, being constituted of polyurethane, this material being naturally hydrophobic.

EXAMPLES

Example 1

Making of a Detector 6 Formed of a Porous Polymer and a Probe Trapped in the Structure of the Polymer 300 mg of 4-(dimethylamino)benzaldehyde (DMABA) are dissolved in 10 ml of methanol. 2 mL of hydrochloric acid 1 M is added to the solution under agitation.

1 g of agarose is dissolved in 20 ml of water at 80° C. under agitation. After dissolution, the solution containing DMABA is added to the agarose solution at 80° C. After returning to the ambient temperature (approximately 25° C.), it is obtained the detector 6 in the form of a whitish gel.

Example 2

Making of a Dressing 1 Containing a Detector 6

A dressing 1 marketed under the mark URGO Discret is used for the detection of indole. This dressing 1 comprises a primary dressing 9 containing a piece of textile gauze and a secondary dressing 10 which is adhesive and transparent.

A drop of 10 μl of the detector 6 synthesized according to the example 1 is previously heated at 80° C. and then deposited onto the primary textile dressing 9 of the dressing 1. While returning at the ambient temperature, the detector 6 absorbed by the textile part of the primary dressing 9 is solidified in the form of a layer of whitish gel.

Test of Detection of Indol

Figure 6:
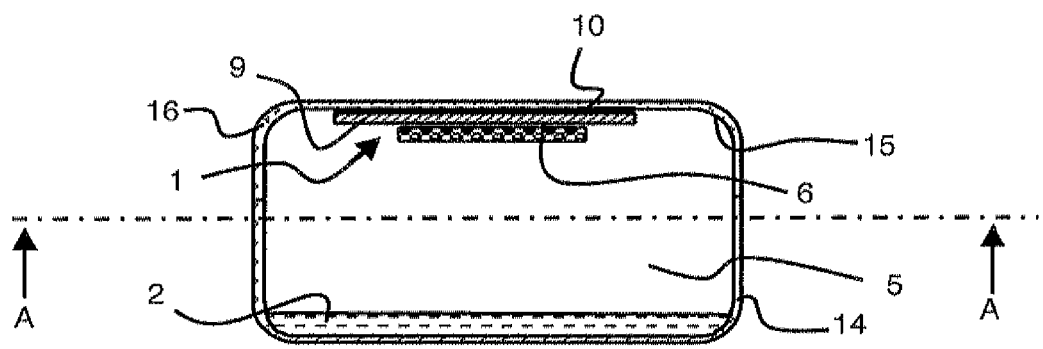
FIG. 6 is a schematic and sectional representation of a test device for detecting indole on a dressing according to the invention.
Figure 7:
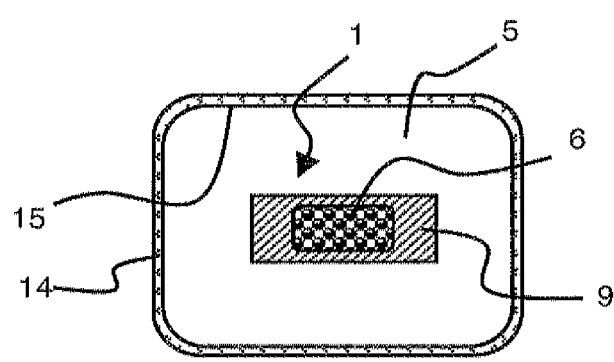
FIG. 7 is a schematic representation of a test device along the axis AA in FIG. 6.

As represented in FIGS. 6 and 7, an aqueous indole solution is prepared at $10^{-1}$ M. 1 ml is placed in a transparent container 14 such as a well plate. The dressing 1 obtained in the example 1 is stuck onto the internal wall 15 of the lid 16 of the well plate 14 via its adhesive part so that the layer formed by impregnation of the detector 6 on the surface of the primary dressing 9 is opposite the indole solution. The detector 6 is not in contact with this indole solution. After 10 minutes at the ambient temperature, the detector 6 becomes pink thus showing the reaction between the indole volatilized in a gas form and the detector 6.

Example 3

Making of a Dressing 1 Containing Two Detectors 6

300 mg of 4(dimethylamino)cinnamaldehyde are dissolved in 10 ml of methanol. 2 ml of hydrochloric acid 1 M is added to the solution under agitation. 1 g of agarose is dissolved in 20 ml of water at 80° C. under agitation. After dissolution, the solution containing DMACA is added to the agarose solution at 80° C. and then, before returning to the ambient temperature, a drop of 30 μl is deposited onto the primary textile dressing 9 of a dressing 1 of the mark URGO Discret, marketed by URGO. The drop is then absorbed by the textile part of the primary dressing 9. After returning to the ambient temperature, it is obtained the detector 6 in the form of an orange-brown gel layer.

The same procedure is carried out with DMABA except for the fact that the detector 6 is deposited onto the same primary dressing 9 of the dressing URGO Discret but at a different place. After returning to the ambient temperature, it is obtained a detector 6 in the form of a layer of whitish gel (detector 6 DMABA/agarose) adjacent to an orange-brown gel layer (detector 6 DMACA/agarose).

Cultures of Bacteria

A colony of a strain *Escherichia coli* ATCC 11775—Indole positive marketed by the company LGC Standards, noted EC5, is pre-cultured in 4 mL of LB medium at 30° C. under agitation during approximately 15 h. A colony on agar LB box is suspended in 4 mL of LB (×2 tubes), agitated and then maintained at a temperature of 30° C. in statics during 15 h.

The same procedure is carried out with two other strains: *Hafnia alvei* ATCC 13337—Indole negative marketed by the company LGC standards, noted HA4, and *Pseudomonas putida* ATCC 12633—Indole negative marketed by the company LGC standards, noted PP6.

Preparation of the Medium Tryptophan/Agar:

The preparation of the liquid medium Tryptophan/agar is carried out by mixing 3.2 g/200 ml of DEV Tryptophan Broth (FLUKA 31406) and 3 g/200 ml of agar (FLUKA 05039) and then by heating the mixture in an autoclave at 121° C. and 2.2 bars during 20 min.

The medium is remove out of the autoclave in a still liquid state i.e. at a temperature comprised between approximately 60° C. and 70° C., and is directly poured into a Petri dish (FALCON 353001, Becton Dickinson, diameter 35×height 10 mm).

Culture in a Liquid

Tubes with the most concentrated pre-culture, OD at 550 nm:

for HA4: OD (⅕x)=0.16, i.e. an effective OD of 0.8;
for EC5: OD (⅕x)=0.25, i.e. an effective OD of 1.25;
for PP6: OD (⅕x)=0.29, i.e. an effective OD of 1.5.

An inoculation is carried out on a basis of ⅕₀ for an OD of 0.7, i.e. a ¹/₇₀ inoculum (60 μL of pre-culture for 4 ml of LB). The temperature at the beginning of the culture is of 37° C., under agitation at 250 rpm.

After a 2 h culture, it is obtained:
HA4: OD (1×)=0.34 i.e. $1.35.10^8$ cfu/ml
EC5: OD (1×)=0.59 i.e. $1.40.10^8$ cfu/ml
PP6: OD (1×)=0.15 i.e. approximately 5.107 cfu/ml For inoculating a dish of DEV Tryptophan/agar, 20 μL culture are spread with an inoculating loop i.e. 1 to 3 million cfu per dish.

Detection Test for Indole

Three dishes 14 were prepared with strains EC5, HA4 and PP6. A dressing 1, according to the example 3, is stuck onto the internal wall 15 of the lid 16 of the Petri dishes 14 containing respectively EC5, HA4 and PP6 so that the detectors 6, DMABA/agarose and DMACA/agarose, do not touch the medium 2 and then each Petri dish 14 is incubated at a temperature of 37° C.

After a 3 h culture at 37° C., it is obtained a change of color for both detectors 6. The detector 6 containing DMACA changes from orange-brown to green and the detector 6 containing DMABA changes from whitish to pink only in the dish 14 containing EC5 (indole positive). It is noted the effectiveness of the detection method for detecting indole resulting from the metabolism of the bacteria of the indole positive type.

Example 4

Making of a Detector 6 Formed of a Porous Polymer Containing Cyclohexanone or Benzaldehyde A solution containing 2.3 ml of tetraethoxysilane with the formula $Si(OC_2H5)_4$ (TEOS), 0.6 mL of water, 3.6 mL of ethanol, 0.1 mL of acetic acid and 1.2 ml of cyclohexanone or benzaldehyde constituting the molecule probe is prepared in a pill machine.

Example 5

Making of a Dressing 1 Containing the Detector 6 According to the Example 4

After homogenization, the solution in the example 4 is deposited onto the primary dressing 9 of a dressing 1 identical to that in the example 2. After absorption of the solution on the textile piece, the dressing 1 is heated at 70° C. during 3 hours. The detector 6 containing the molecule probe is obtained after drying with the ambient air, in the form of a solid and porous monolayer.

Detection of 2'-Aminoacetophenone

An aqueous solution of 2'-aminoacetophenone is prepared with 0.5 M. 5 ml are placed in a bottle provided with a lid. The dressing 1 obtained in the example 5 is stuck onto the internal wall of the lid in order to direct the primary dressing 9 containing the detector 6, opposite the solution of 2'-aminoacetophenone, without however bringing the detector 6 in contact with the solution of 2'-aminoacetophenone. After 72 minutes at 37° C., the detector 6 becomes yellow if the molecule probe is cyclohexanone or orange if the molecule probe is benzaldehyde. Three pilot tests were carried out on a purely comparative basis according to an identical procedure. The results obtained are given in the table below:

| N° | Solution | Molecule probes | Detector coloring |
| --- | --- | --- | --- |
| 1 | 2'-aminoacetophenone 0.5M | — | — |
| 2 | 2'-aminoacetophenone 0.5M | cyclohexanone | yellow |
| 3 | Water | cyclohexanone | — |
| 4 | 2'-aminoacetophenone 0.5M | benzaldehyde | orange |
| 5 | Water | benzaldehyde | — |

It is noted that the pilot tests remain colorless whereas the bottles 2 and 4 detect indeed the presence of 2'-aminoacetophenone.

It is noted that the pilot tests remain colorless whereas the bottles 2 and 4 detect indeed the presence of 2'-aminoacetophenone.

The present invention is not limited to the examples and particular embodiments, which are purely illustrative. Variations are possible within the framework of the claimed protection, in particular, the dressing 1 can comprise several layers in particular hydrophilic polymer or textile layers, ensuring in particular a mechanical resistance and/or improving the conditions of detection of the metabolite(s). In addition, when the bodily fluid is sweat, the element of confinement can be different from a dressing.

The finality of the detection method according to this invention is to indicate the presence or not of one or more analytes in a bodily fluid. The detection method has the advantage of a sensitive and discriminating detection for the different analytes to be analyzed. The method allows, in particular by observation or not of a signal, a qualitative and advantageously quantitative analysis of the analyte, with a high sensitivity and a low risk of false positive results.

The detection method is simple to implement, rapid and avoids any contamination of the bodily fluid. Indeed, the dressing allowing the implementation of the method contains a detector which is not in contact with the bodily fluid and does not consequently modify the composition of the bodily fluid. In particular, the dressing applied to a wound does not disturb the healing and avoids any risk of toxicity or modification of the coloring of the bodily fluid. In addition, the signal detected by the detection method can provide a relevant intermediate result indicating the need for changing the dressing.

The invention claimed is:

1. A method for detecting an analyte in a bodily liquid fluid, comprising:
    placing a dressing in contact with a human or animal skin, said skin excreting said bodily liquid fluid, said bodily liquid fluid including said analyte, said dressing including at least a detector, said detector being located above the human or animal skin;
    waiting for said analyte to either degrade or metabolize, and in doing so release a Volatile Organic Compound (VOC), said VOC released from the analyte being in a liquid form;
    waiting for said liquid form of the VOC to evaporate into a gaseous organic compound; and
    detecting said gaseous organic compound with said detector, wherein
        said detector is an optical detector, where the optical detector is configured such that the presence of a gaseous form of the VOC modifies optical properties of the optical detector, and
        said detector does not contact said bodily liquid fluid.

2. The method of claim 1, wherein said analyte is a bacteria.

3. The method of claim 1, wherein said optical detector is a chromogene detector, which color changes when contacting said gaseous form of the VOC.

4. The method of claim 1, wherein said optical detector is a fluorogene detector, which produces a fluorescent emission when contacting said gaseous form of the VOC.

5. The method of claim 1, wherein said detector includes a probe, which is specific
    to a predetermined Volatile Organic Compound released by the analyte, or
    to a predetermined class of Volatile Organic Compounds released by the analyte.

6. The method of claim 1, wherein said detector is isolated from said bodily fluid by a protection element, which prevents any contact between said bodily fluid and said detector.

7. The method of claim 1, wherein
    said detector includes
        a support, which is permeable to the gaseous form of the VOC, and
        a probe, which is incorporated into the support, said probe being sensitive to the gaseous form of the VOC.

8. The method of claim 1, wherein said detector comprises a probe, and said gaseous organic compound is detected via the probe selectively reacting with said gaseous organic compound.

9. A method for detecting an analyte in a bodily liquid fluid, comprising:
    placing a dressing in contact with a human or animal skin, said skin excreting said bodily liquid fluid, said bodily liquid fluid including said analyte, said dressing including at least a detector, said detector being located above the human or animal skin,
    degrading or metabolizing said analyte to release a Volatile Organic Compound (VOC), said VOC being in a liquid form; and
    detecting a gaseous form of the VOC with said detector, when said liquid form of the VOC evaporates into said gaseous form of the VOC, wherein
        said detector is an optical detector, where the optical detector is configured such that the presence of a gaseous form of the VOC modifies optical properties of the optical detector, and
        said detector does not contact said bodily liquid fluid.

10. The method of claim 1, wherein the detector includes a probe, where the probe is specific
    to a predetermined Volatile Organic Compound released by the analyte, or
    to a predetermined class of Volatile Organic Compounds released by the analyte, and
    the probe is incorporated into the support by trapping, by adsorption or by covalent bonding.

11. The method of claim 10, wherein the probe has one or more functions configured to interact with the predetermined Volatile Organic Compound released by the analyte such that, once bound to the predetermined Volatile Organic Compound released by the analyte, the probe produces an optically detectable signal.

12. The method of claim 11, wherein the detection of said gaseous organic compound with said detector comprises forming an absorbing or fluorescent compound by reacting the probe with the gaseous form of the VOC.

13. The method of claim 1, wherein the VOC in a liquid form that is released by the analyte is selected from the group consisting of ethanol, acetone, acetaldehyde, acetic acid, dimethyl sulfide, methane thiol, indole, aminoacetophenone, trimethylamine, hexanal, methanol, putrescine, cadaverine, $CH_3SH$ and cyclohexanone.

14. The method of claim 1, wherein said detector includes a probe selected from the group consisting of 4-aminopent-3-in-2-one, dimethylaminobenzaldehyde, 4-dimethylaminocinnamaldehyde, cyclohexanone and acetaldehyde.

15. The method of claim 1, wherein
- said detector includes a probe comprising dimethylaminobenzaldehyde, and the gaseous organic compound is an indole;
- said detector includes a probe comprising 4-dimethylaminocinnamaldehyde, and the gaseous organic compound is an indole;
- said detector includes a probe comprising 4-aminopent-3-in-2-one, and the gaseous organic compound is an aldehyde;
- said detector includes a probe comprising cyclohexanone, and the gaseous organic compound is 2'aminoacétophénone; or
- said detector includes a probe comprising an aldehyde, and the gaseous organic compound is 2'aminoacétophénone.

* * * * *